United States Patent [19]

Stödberg et al.

[11] 4,167,675
[45] Sep. 11, 1979

[54] X-RAY COLLIMATOR COMPRISING LIGHT BEAM LOCALIZER WITH LENS SYSTEM

[75] Inventors: Lars Stödberg, Stenhamra; Hans Sjöström, Spanga, both of Sweden

[73] Assignee: Siemens Aktiengesellschaft, Berlin & Munich, Fed. Rep. of Germany

[21] Appl. No.: 804,536

[22] Filed: Jun. 8, 1977

[30] Foreign Application Priority Data

Jul. 22, 1976 [DE] Fed. Rep. of Germany ....... 2623213

[51] Int. Cl.$^2$ .............................................. A61B 6/08
[52] U.S. Cl. ..................................... 250/491; 250/513
[58] Field of Search ............................... 250/491, 513

[56] References Cited

U.S. PATENT DOCUMENTS

| 2,474,422 | 6/1949 | Hollstein | 250/491 |
| 2,667,586 | 1/1954 | Oswald | 250/513 |
| 4,060,733 | 11/1977 | Franke | 250/491 |

FOREIGN PATENT DOCUMENTS

| 903085 | 1/1945 | France . | |
| 2275111 | 9/1976 | France . | |
| 69345 | 8/1951 | Netherlands . | |
| 1313296 | 4/1973 | United Kingdom | 250/491 |

*Primary Examiner*—Alfred E. Smith
*Assistant Examiner*—T. N. Grigsby
*Attorney, Agent, or Firm*—Hill, Van Santen, Steadman, Chiara & Simpson

[57] ABSTRACT

In the illustrated embodiment, the light source utilized to mark the x-ray beam is a halogen lamp with a small focus, an optical lens system being provided for concentrating the light beam on an operative portion of a light reflective mirror so as to amplify the light intensity of the beam reflected by the mirror and lying within the fully opened pairs of x-ray opaque plates. The mirror is shown disposed at approximately 45° diagonally relative to the collimator longitudinal axis with the axis of the light source and optical system extending approximately perpendicularly to the collimator longitudinal axis. The mirror is located between sets of close-to-focus plates and sets of remote-from-focus plates so as to provide a reflected diverging light beam of frusto-pyramidal configuration conforming with the pyrmidal beam shape for x-ray energy defined by the sets of plates. As the plates are adjusted by a scissors action in respective planes, the transmitted light beam is adjusted so as to conform with the transmitted x-ray beam.

3 Claims, 2 Drawing Figures

X-RAY COLLIMATOR COMPRISING LIGHT BEAM LOCALIZER WITH LENS SYSTEM

BACKGROUND OF THE INVENTION

The invention relates to an x-ray collimator (primary radiation diaphragm) comprising at least two pairs of collimator plates, staggered 90°, wherein the plates of each plate pair are commonly adjustable symmetrically to the longitudinal axis of the collimator, and comprising a light-beam localizer (or light visor) for rendering visible the collimated field, exhibiting a light source which emits a beam of light bounded by the collimator plates.

An x-ray apparatus equipped with a light beam localizer arrangement for marking the extent of the x-ray beam is known from the U.S. Pat. No. 2,955,205. The light source radiates onto an x-ray-transmissive mirror disposed in the path of the x-rays and inclined in relation to the central ray of the x-radiation. The disadvantage of this light beam localizer consists in that the light rays of the light source are directed not only onto the mirror, but that they issue from the light source in all directions. Therefore, a light source with a high power must be employed which is expensive and susceptible to failure, and which entails cooling problems.

SUMMARY OF THE INVENTION

The object which is the basis of the invention consists in producing an x-ray collimator of the type initially cited which can operate with a low-power light source.

In accordance with the invention, this object is achieved by virtue of the fact that there is arranged directly before the light source and in its radiation path, an optical lens system for the purpose of concentrating its radiation and for the purpose of amplifying the useful radiation intensity. In the inventive collimator, a satisfactory visual indication of the collimated field is possible with a third of the lamp power of the known light beam localizer.

In an x-ray collimator wherein two collimator plate pairs which are staggered 90° lie close-to-focus when the collimator is mounted onto an x-ray housing, and wherein two further collimator plate pairs, which are also staggered 90°, lie remote-from-focus when the collimator is installed, and wherein all plates are adjustable in such a manner that, in the installed state, the collimated pyramid has its apex lying in the focus of the x-ray tube, a further development of the invention is to be found in that a mirror is arranged between the close-to-focus and the remote-from-focus collimator plate pairs, approximately 45° diagonally relative to the collimator longitudinal axis, toward which the light source with its optical system is aligned in such a fashion that the central light ray runs approximately perpendicularly to the collimator longitudinal axis.

Other objects, features and advantages of the present invention will be apparent from the following detailed description taken in connection with the accompanying sheets of drawings.

DETAILED DESCRIPTION

Figure 1:
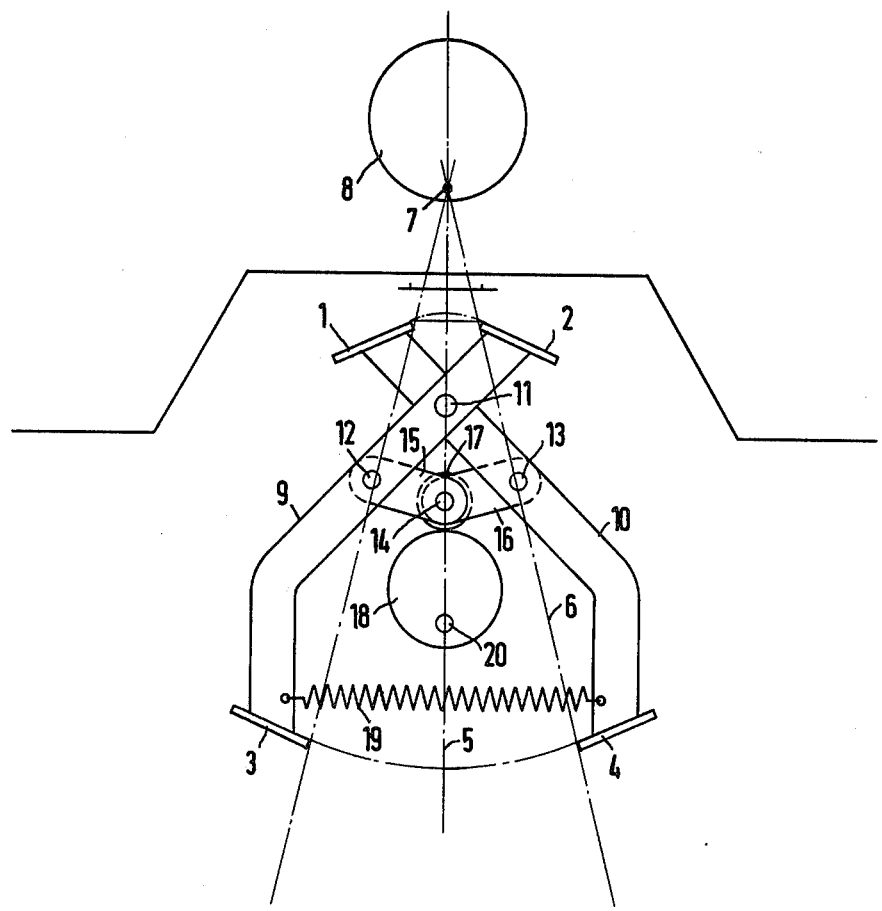
FIG. 1 illustrates an x-ray collimator for the purpose of explaining the invention.

The x-ray collimator consists of two pairs of collimator plates lying close-to-focus, staggered 90°, and also consists of two pairs of collimator plates lying remote-from-focus, which are likewise staggered 90°. In FIG. 1, only one pair of parallel close-to-focus collimator plates 1, 2 of the two pairs and one pair of parallel remote-from-focus collimator plates 3, 4 of the two pairs are represented. The pairs 1, 2 and 3, 4 are commonly adjustable symmetrically to the longitudinal axis 5 of the collimator in such a manner that the collimated pyramid 6 has its apex lying in the focus 7 of x-ray tube 8. Each close-to-focus collimator plate 1, 2, and the remote-from-focus collimator plate 3, 4, which is parallel thereto and opposite in relation to the longitudinal axis 5 of the collimator, is mounted on one lever 9, 10. The levers 9 and 10 are pivotally mounted in scissors-like fashion about a pivot pin 11 lying between the pairs of collimator plates 1, 2 and 3, 4, and parallel thereto. This pivot pin 11 is common to all four parallel collimator plates 1 through 4. The length of the lever arms is dependent upon the distance of focus 7 from the lever pivot pin 11, and is thus dependent upon the position of the apex of pyramid 6.

Also provided on the two levers 9, 10, which are connected in a scissors-like fashion, there are two arms 15, 16, symmetrically linked to said levers at pivot pins 12, 13, and interconnected in an articulated fashion at pivot pin 14.

In order to adjust the pairs of collimator plates 1, 2, and 3, 4, a roller 17 is arranged such that it is rotatable about pivot pin 14. This roller runs on a cam disc 18 and is resiliently pressed against the latter. Tensioning of the levers 9, 10, proceeds by means of a tension spring 19 which is arranged between them. A non-illustrated electric motor is provided for the drive of the cam disc 18, said motor driving cam disc 18 via shaft 20. In the position of the cam disc 18 as shown in FIG. 1, the collimator plates 1, 2 and 3, 4 are completely open. Upon rotating cam disc 18 by means of the electric motor, the pairs of collimator plates 1, 2 and 3, 4 are moved toward one another until the desired position has been reached. Guidance means are provided which confine roller 17 to a straight line path parallel to the collimator axis 5 during the collimator adjustment. An adjustment- and support-mechanism in accordance with FIG. 1 is also present for the other, non-illustrated pairs of collimator plates which define the other two lateral boundaries of the pyramid 6. The illustration in FIG. 1 is equally applicable to the other pairs of plates.

Figure 2:
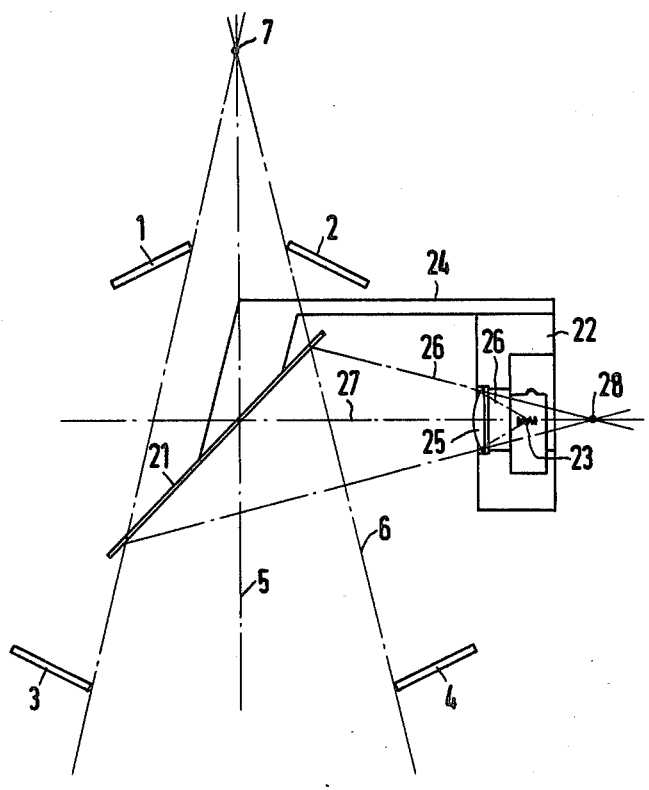
FIG. 2 is a schematic diagram showing the x-ray collimator according to FIG. 1 with an inventive optical lens system for use in visually indicating the adjustment of the collimator.

FIG. 2 illustrates an x-ray transmissive light reflector 21 arranged between the close-to-focus and the remote-from-focus pairs of collimator plates 1, 2, and 3, 4, the reflector or mirror 21 being arranged diagonally at an angle of approximately 45° relative to the collimator longitudinal axis 5. Mirror 21 is connected to a housing 22 for a light source 23 by a transverse arm 24 which lies outside the maximum collimated pyramid 5 and engages an extension of mirror 21 which is offset from the operative x-ray transmissive portion of the mirror. The housing 22 is, in turn, mounted to a non-illustrated framework of the x-ray collimator. In housing 22, directly before the light source 23, there is arranged in the radiation path of said light source an optical lens system 25 for the purpose of concentrating its beam of rays 26 and for the purpose of amplifying the radiation intensity impinging on the operative x-ray transmissive portion of mirror 21, said optical lens system 25 being arranged such that the beam 26, for all practical purposes, does not radiate beyond the operative portion of mirror 21; thus, that it has a virtual focus 28 on the side of light source 23 remote from mirror 21. The light source 23, with its optical lens system 25, is so aligned with mirror 21 that the central light ray 27 runs approximately perpendicularly to the collimator longitudinal axis 5. The light beam issuing from the collimator has the same dimensions as the x-ray beam and is bounded by the remote-from-focus pairs of collimator plates such as 3 and 4.

The light ray source 23 is a halogen lamp with a small focus. Through the use of an optical lens system in conjunction with a light source having a low power, a good field illumination can be obtained. Due to the low power of the light source, no cooling problems arise. In addition, the lower power requirement is advantageous in the case of a battery power supply.

It will be apparent that many modifications and variations may be effected without departing from the scope of the novel concepts and teachings of the present invention.

We claim as our invention:

1. An x-ray collimator comprising at least two pairs of collimator plates, staggered 90°, wherein the plates of each pair of collimator plates are commonly adjustable symmetrically to the longitudinal axis of the collimator, and comprising a light beam localizer for the purpose of rendering visible the collimated field, including a light source which produces a light beam bounded by the collimator plates, characterized in that there is arranged directly before the light source and in the radiation path of said light source, an optical lens system for the purpose of concentrating its radiation and for the purpose of amplifying the radiation intensity of said light beam, and wherein two pairs of collimator plates, staggered 90°, lie close-to-focus when the collimator is mounted onto an x-ray tube housing, and wherein two additional pairs of collimator plates, also staggered 90°, lie remote-from-focus when the collimator is installed, and wherein all plates are adjustable such that, in the installed state, the collimated pyramid has its apex lying at the focus of the x-ray tube, characterized in that a mirror is arranged between the close-to-focus and the remote-from-focus pairs of collimator plates, said mirror being arranged diagonally at an angle of approximately 45° relative to the longitudinal axis of the collimator, the light source with its optical lens system being so aligned to said mirror that the central light ray runs approximately perpendicularly to the collimator longitudinal axis.

2. A collimator according to claim 1, characterized in that the mirror is connected to the housing of the light source by a transverse arm which is clear of the collimated pyramid.

3. A collimator according to claim 1, characterized in that the light source is a halogen lamp, the lens system defining a virtual focus offset from the halogen lamp in the direction away from said mirror.

* * * * *